(12) United States Patent
Akagane

(10) Patent No.: US 9,345,505 B2
(45) Date of Patent: May 24, 2016

(54) ULTRASONIC TRANSMITTING UNIT

(71) Applicant: OLYMPUS MEDICAL SYSTEMS CORP., Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/470,649

(22) Filed: Aug. 27, 2014

(65) Prior Publication Data

US 2015/0080927 A1   Mar. 19, 2015

Related U.S. Application Data

(63) Continuation of application No. PCT/JP2013/067895, filed on Jun. 28, 2013.

(60) Provisional application No. 61/697,642, filed on Sep. 6, 2012.

(51) Int. Cl.
*A61B 17/32* (2006.01)
*A61B 17/22* (2006.01)

(52) U.S. Cl.
CPC ............ *A61B 17/320068* (2013.01); *A61B 2017/22015* (2013.01)

(58) Field of Classification Search
CPC ............ A61B 17/320068; A61B 2017/22015; A61B 2017/320072; A61B 2017/042; A61B 17/22012; A61B 17/2202; A61B 2017/22014; A61F 2002/30065
See application file for complete search history.

(56) References Cited

U.S. PATENT DOCUMENTS

| | | | |
|---|---|---|---|
| 4,869,715 A * | 9/1989 | Sherburne | 604/22 |
| 6,582,392 B1 * | 6/2003 | Bennett et al. | 604/22 |
| 2003/0065263 A1 * | 4/2003 | Hare et al. | 600/439 |
| 2009/0143796 A1 * | 6/2009 | Stulen et al. | 606/169 |
| 2015/0045701 A1 * | 2/2015 | Akagane | 601/2 |
| 2015/0057577 A1 * | 2/2015 | Akagane | 601/2 |

FOREIGN PATENT DOCUMENTS

| | | |
|---|---|---|
| JP | A-2-98345 | 4/1990 |
| JP | H02-286149 A | 11/1990 |
| JP | A-6-343648 | 12/1994 |
| JP | A-2000-506431 | 5/2000 |
| JP | A-2005-94552 | 4/2005 |
| JP | A-2010-535089 | 11/2010 |

OTHER PUBLICATIONS

International Search Report issued in PCT/JP2013/067895 mailed Sep. 24, 2013 (with translation).

* cited by examiner

*Primary Examiner* — Alexander Orkin
(74) *Attorney, Agent, or Firm* — Oliff PLC

(57) ABSTRACT

An ultrasonic transmitting unit includes a first vibrating section and second vibrating section vibrating at the same predetermined frequency with respect to each other. The ultrasonic transmitting unit includes a relay portion transmitting the ultrasonic vibration toward a first transmitting direction from the first vibrating section to the second vibrating section and positioned at a position corresponding to one of an antinode position of the vibration in the first vibrating section and different from an antinode position and a node position of the vibration in the second vibrating section, and a non-contact vibrating portion extending in a second vibrating section from the relay portion toward a second transmitting direction without contact with the first vibrating section.

8 Claims, 13 Drawing Sheets

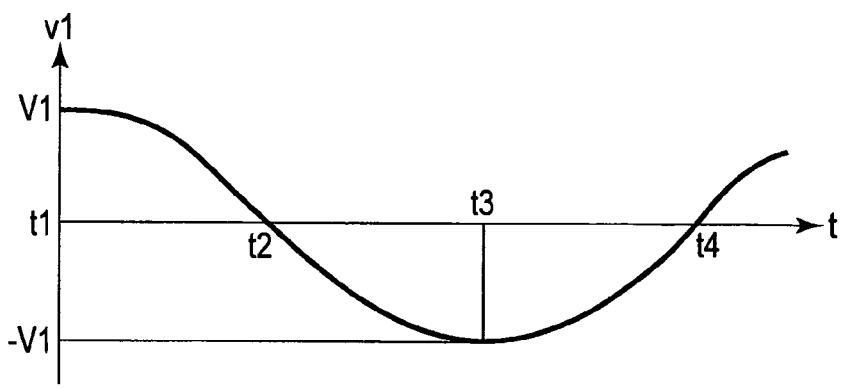
F I G. 10
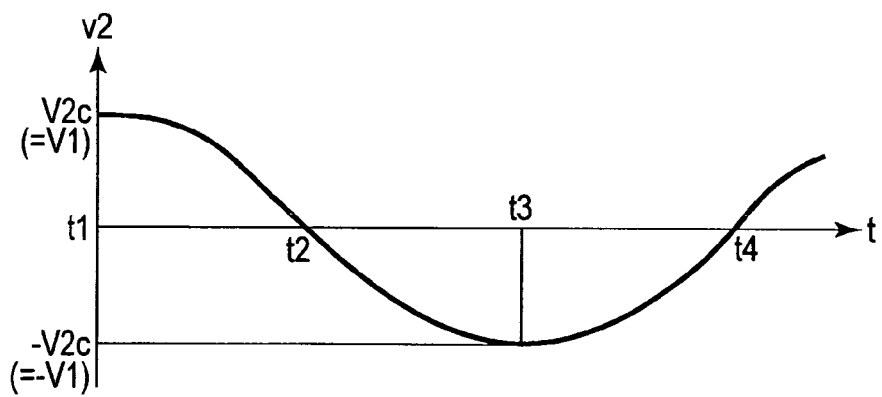
F I G. 11
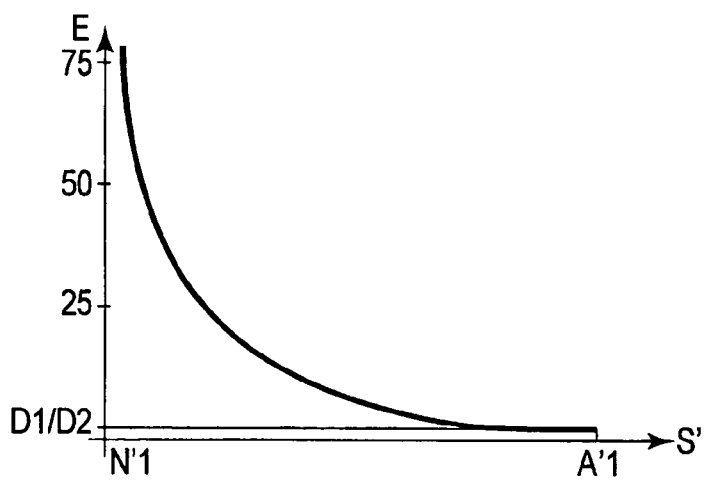
F I G. 12

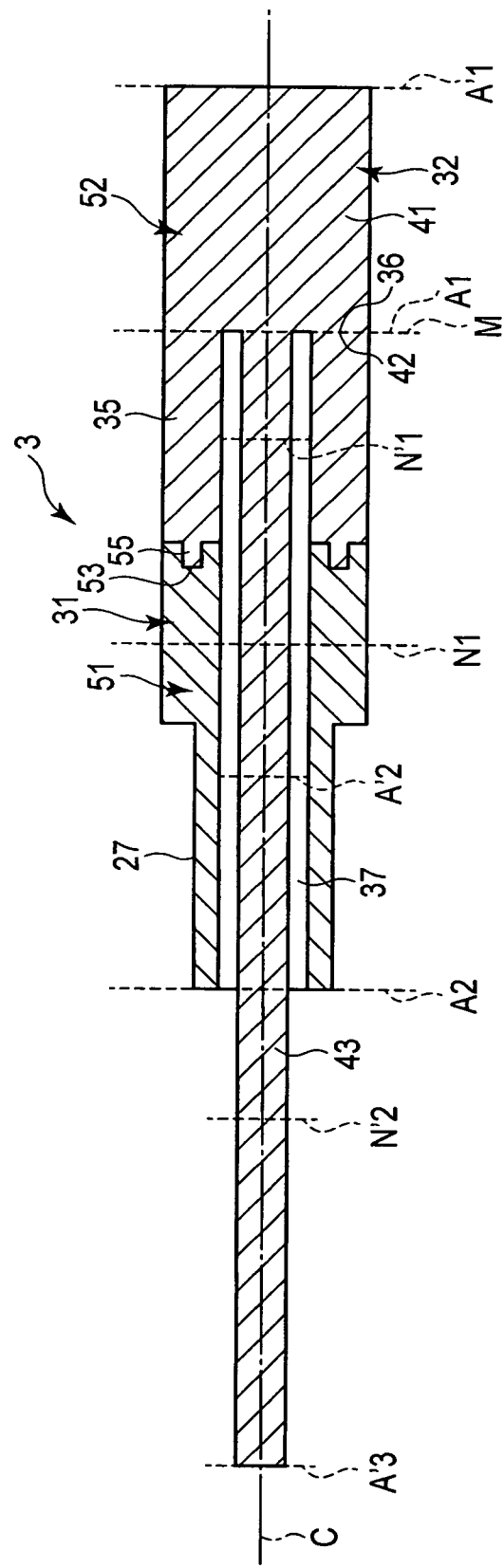
F I G. 13

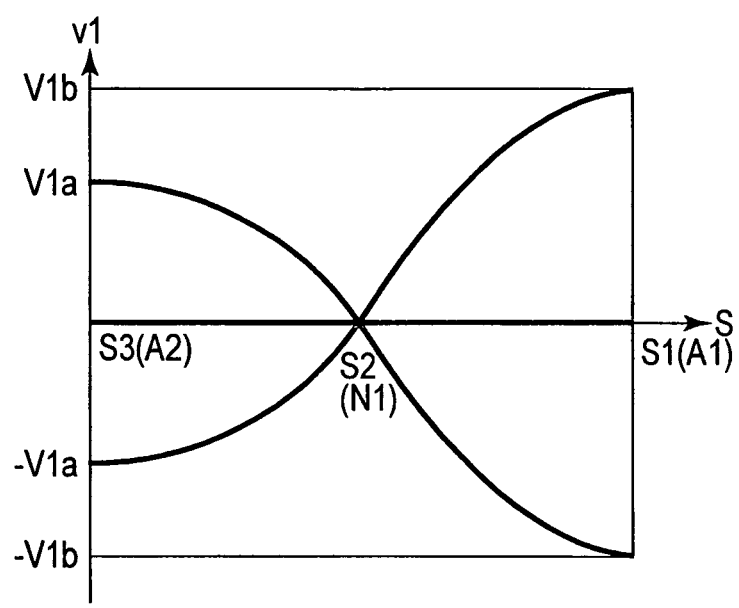
F I G. 16

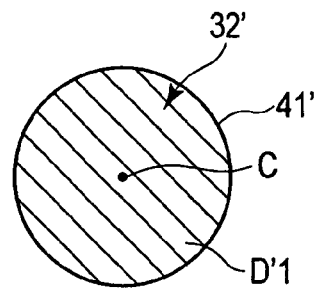
F I G. 19
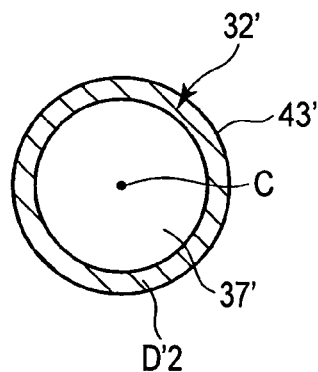
F I G. 20
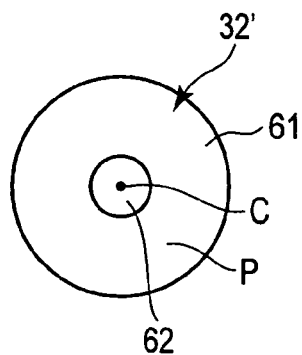
F I G. 21

ULTRASONIC TRANSMITTING UNIT

CROSS-REFERENCE TO RELATED APPLICATIONS

This is a Continuation application of PCT Application No. PCT/JP2013/067895, filed Jun. 28, 2013 and based upon and claiming the benefit of priority from prior U.S. Provisional Application No. 61/697,642, filed Sep. 6, 2012, the entire contents of which are incorporated herein by reference.

BACKGROUND OF THE INVENTION

1. Field of the Invention

The present invention relates to an ultrasonic transmitting unit which extends along a longitudinal axis and which is configured to transmit an ultrasonic vibration from a proximal direction toward a distal direction.

2. Description of the Related Art

Ultrasonic transmitting units extending along a longitudinal axis are disclosed in the specification of Jpn. PCT National Publication No. 2010-535089 and the specification of Jpn. PCT National Publication No. 2000-506431. Each of the ultrasonic transmitting units includes a columnar portion and an ultrasonic probe connected to a distal direction side of the columnar portion. An ultrasonic generating portion such as an ultrasonic vibrator which is configured to generate an ultrasonic vibration is attached to the columnar portion. The ultrasonic vibration generated in the ultrasonic generating portion is transmitted from a proximal direction toward a distal direction through the columnar portion and the ultrasonic probe.

Furthermore, in each of the ultrasonic transmitting units, the columnar portion is provided with a sectional area changing portion (a horn portion) in which a sectional area perpendicular to the longitudinal axis changes. Due the sectional area changing portion, an amplitude of the ultrasonic vibration increases.

BRIEF SUMMARY OF THE INVENTION

According to one aspect of the invention, an ultrasonic transmitting unit includes that: an ultrasonic vibrator which is configured to generate an ultrasonic vibration; a first vibrating section which is configured to transmit the ultrasonic vibration generated by the ultrasonic vibrator toward a first transmitting direction, and thereby configured to perform a vibration having an antinode position and a node position at a predetermined frequency; a second vibrating section which is configured to perform a vibration having an antinode position and a node position at the same predetermined frequency as in the first vibrating section when the ultrasonic vibration is transmitted from the first vibrating section; a relay portion which relays between the first vibrating section and the second vibrating section, and which is configured to transmit the ultrasonic vibration toward the first transmitting direction from the first vibrating section to the second vibrating section, the relay portion being positioned at a position corresponding to one of the antinode position of the vibration in the first vibrating section and different from the antinode position and the node position of the vibration in the second vibrating section in a state that the first vibrating section and the second vibrating section vibrate at the predetermined frequency; a non-contact vibrating portion which is provided in the second vibrating section, and which extends from the relay portion toward a second transmitting direction side in a state that the non-contact vibrating portion is not in contact with the first vibrating section, when an opposite direction with respect to the first transmitting direction is a second transmitting direction; and a treatment portion which is provided in the non-contact vibrating portion of the second vibrating section, and which is formed in a second-transmitting-direction-side end portion of the second vibrating section, the treatment portion being configured to treat a treatment object by use of the ultrasonic vibration.

According to one another aspect of the invention, an ultrasonic transmitting unit which is formed by connecting a first transmitting member and a second transmitting member, the first transmitting member being configured to perform a vibration having an antinode position and a node position at a predetermined frequency by an ultrasonic vibration transmitted toward a first transmitting direction, the second transmitting member being configured to perform a vibration having an antinode position and a node position at the same predetermined frequency as in the first transmitting member by the ultrasonic vibration transmitted from the first transmitting member, wherein the first transmitting member includes: a first relay portion which is positioned at a position corresponding to one of the antinode position of the vibration in the first transmitting member in a state that the first transmitting member vibrates at the predetermined frequency, and which abuts on the second transmitting member connected to the first transmitting member, and the second transmitting member includes: a second relay portion which is positioned at a position different from the antinode position and the node position of the vibration in the second transmitting member in a state that the second transmitting member vibrates at the predetermined frequency, and which abuts on the first relay portion of the first transmitting member connected to the second transmitting member, and the second relay portion being configured to transmit the ultrasonic vibration toward the first transmitting direction from the first relay portion of the first transmitting member to the second transmitting member; a non-contact vibrating portion which extends from the second relay portion toward a second transmitting direction side in a state that the non-contact vibrating portion is not in contact with the first transmitting member in the second transmitting member in which the second relay portion abuts on the first relay portion of the first transmitting member, when an opposite direction with respect to the first transmitting direction is a second transmitting direction; and a treatment portion which is provided in the non-contact vibrating portion of the second transmitting member, and which is formed in a second-transmitting-direction-side end portion of the second transmitting member, the treatment portion being configured to treat a treatment object by use of the ultrasonic vibration.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 10 is a schematic view showing a change of the first vibration with time at a relay antinode position of the first vibrating section, when the ultrasonic transmitting unit according to the first embodiment vibrates;

FIG. 11 is a schematic view showing a change of the second vibration with time at a middle position of the second vibrating section, when the ultrasonic transmitting unit according to the first embodiment vibrates;

FIG. 12 is a schematic view showing an enlargement ratio of a second amplitude at a most distal antinode position of the second vibration with respect to a first amplitude at a first antinode position of the first vibration, when a position of the middle position is changed along the longitudinal axis in the second vibrating section according to the first modification;

FIG. 13 is a sectional view schematically showing a configuration of an ultrasonic transmitting unit according to a first modification;

FIG. 16 is a schematic view showing a change of a first vibration in accordance with a change of a position along a longitudinal axis in a first vibrating section, when the ultrasonic transmitting unit according to the third modification vibrates;

FIG. 19 is a sectional view along the line 19-19 of FIG. 18;

FIG. 20 is a sectional view along the line 20-20 of FIG. 18; and

FIG. 21 is a schematic view of FIG. 17 seen from a distal direction.

DETAILED DESCRIPTION OF THE INVENTION

First Embodiment

Figure 1:
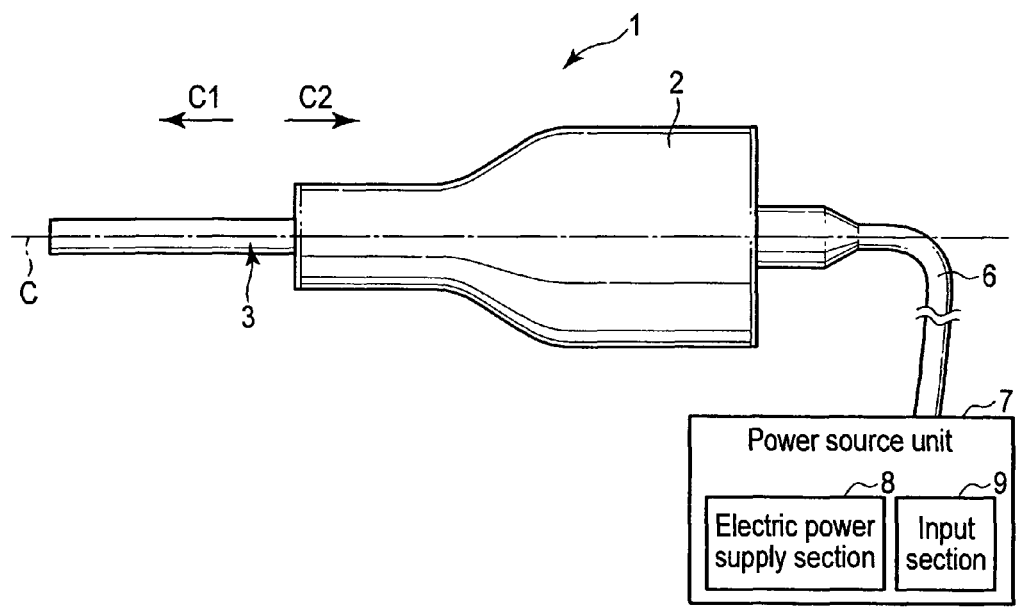
FIG. 1 is a schematic view showing an ultrasonic treatment device according to a first embodiment of the present invention.

A first embodiment of the present invention will be described with reference to FIG. 1 to FIG. 12. FIG. 1 is a view showing an ultrasonic treatment device 1 of the present embodiment. As shown in FIG. 1, the ultrasonic treatment device 1 has a longitudinal axis C. Here, one of two directions parallel to the longitudinal axis C is a distal direction (a direction of an arrow C1 of FIG. 1), and an opposite direction with respect to the distal direction is a proximal direction (a direction of an arrow C2 of FIG. 1). The ultrasonic treatment device 1 includes a vibrator case 2 and an ultrasonic transmitting unit 3 extending along the longitudinal axis C.

The vibrator case 2 is connected to one end of a cable 6. The other end of the cable 6 is connected to a power source unit 7. The power source unit 7 includes a current supply section 8 and an input section 9.

Figure 2:
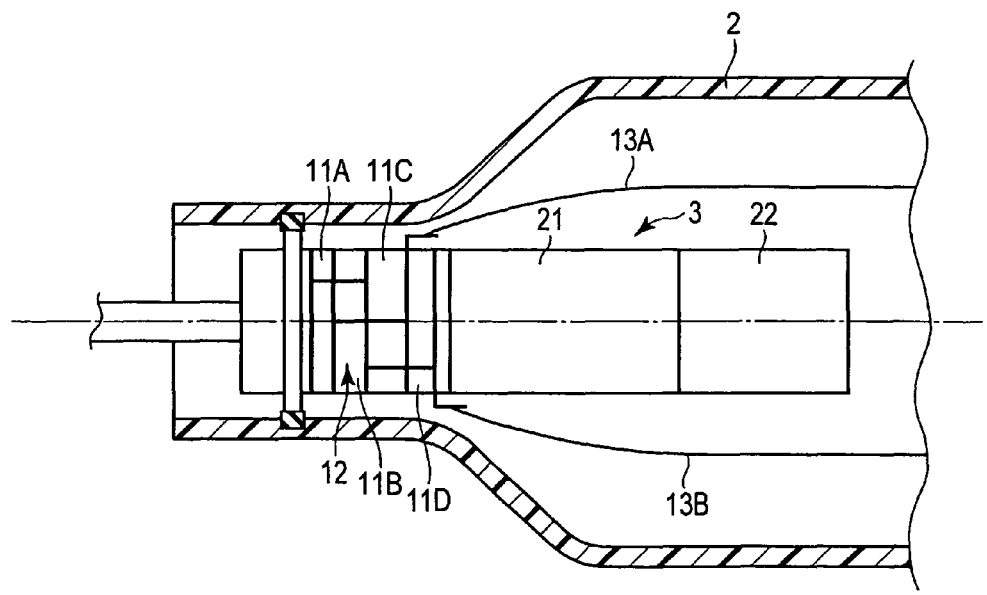
FIG. 2 is a sectional view schematically showing an internal configuration of a vibrator case according to the first embodiment.

FIG. 2 is a view showing an internal configuration of the vibrator case 2. As shown in FIG. 2, in the oscillator case 2, there is disposed an ultrasonic vibrator 12 as an ultrasonic generating portion including piezoelectric elements 11A to 11D which are configured to convert a current into an ultrasonic vibration. The ultrasonic oscillator 12 is attached to the ultrasonic transmitting unit 3. The ultrasonic vibrator 12 is connected to one end of each of electric wiring lines 13A, 13B. The electric wiring lines 13A, 13B pass through the cable 6, and the other end of each electric wiring line is connected to the current supply section 8 of the power source unit 7. The electric power supply section 8 supplies the current to the ultrasonic vibrator 12 via the electric wiring lines 13A, 13B, and the ultrasonic vibration is thereby generated in the ultrasonic oscillator 12.

Figure 3:
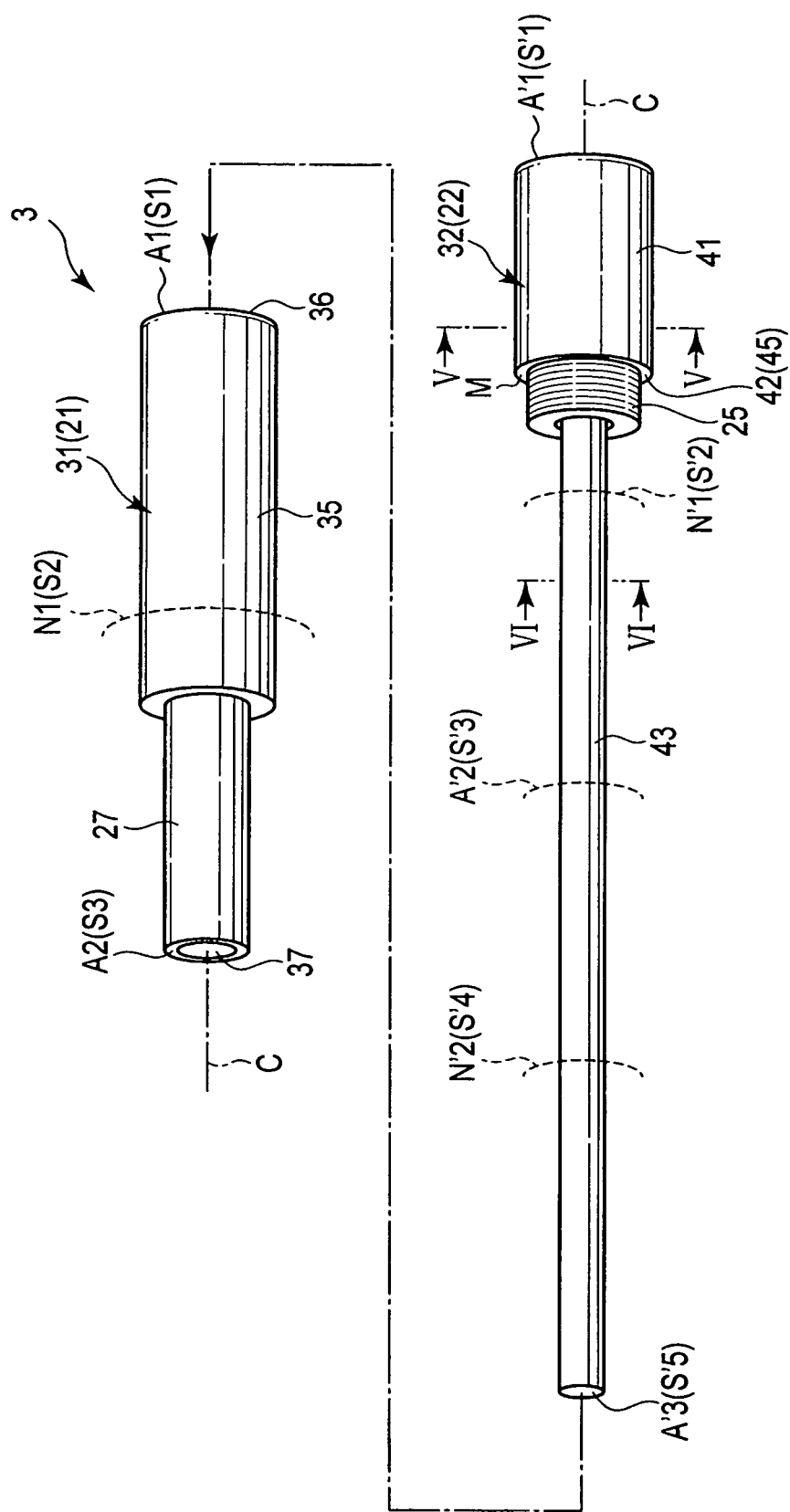
FIG. 3 is a perspective view schematically showing a configuration of an ultrasonic transmitting unit according to the first embodiment.
Figure 4:
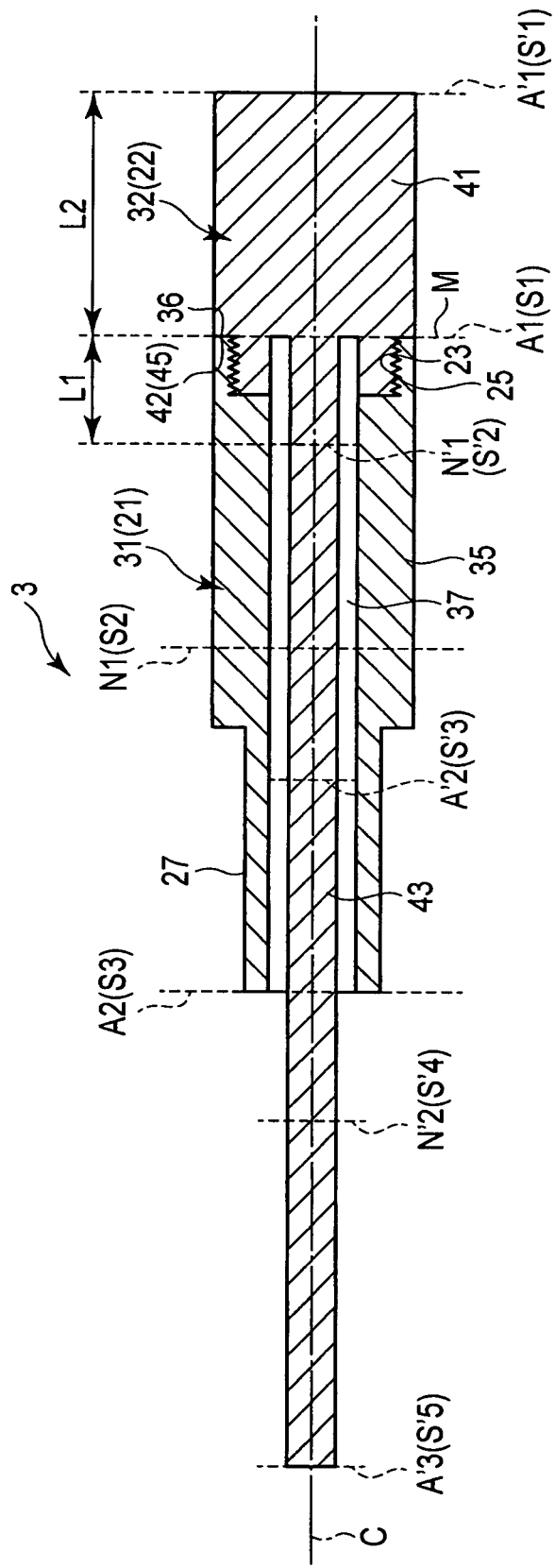
FIG. 4 is a sectional view schematically showing a configuration of an ultrasonic transmitting unit according to the first embodiment.

FIG. 3 and FIG. 4 are views showing the ultrasonic transmitting unit 3. As shown in FIG. 3 and FIG. 4, the ultrasonic transmitting unit 3 includes a first vibration transmitting member 21 and a second vibration transmitting member 22. The second vibration transmitting member 22 is a so-called ultrasonic probe, and a proximal end of the second vibration transmitting member 22 becomes a proximal end of the ultrasonic transmitting unit 3. Furthermore, a distal end of the second vibration transmitting member 22 becomes a distal end of the ultrasonic transmitting unit 3. An internal thread portion 23 is formed in a proximal portion of the first vibration transmitting member 21. Furthermore, an external thread portion 25 is formed in the second vibration transmitting member 22. The internal thread portion 23 is screwed to the external thread portion 25, and the first vibration transmitting member 21 is thereby attached to the second vibration transmitting member 22. Furthermore, the first vibration transmitting member 21 is attached to the vibrator case 2.

In the first vibration transmitting member 21, a vibrator attaching portion 27 is provided. Members constituting the ultrasonic oscillator 12, for example, the piezoelectric elements 11A to 11D, are attached to the vibrator attaching portion 27, and the ultrasonic vibrator 12 which is the ultrasonic generating portion is thereby attached to the first vibration transmitting member 21. When the ultrasonic vibrator 12 is attached to the first vibration transmitting member 21, the ultrasonic vibration generated in the ultrasonic vibrator 12 is transmitted to the ultrasonic transmitting unit 3. Then, in the ultrasonic transmitting unit 3, the ultrasonic vibration is transmitted from the first vibration transmitting member 21 to the second vibration transmitting member 22. The ultrasonic transmitting unit 3 can transmit the ultrasonic vibration in the directions parallel to the longitudinal axis C. In the ultrasonic transmitting unit 3, the ultrasonic vibration is transmitted, and the ultrasonic transmitting unit 3 thereby performs a longitudinal vibration in which a vibrating direction and a transmitting direction are parallel to the longitudinal axis C.

The ultrasonic transmitting unit 3 includes a first vibrating section 31 which is configured to perform a first vibration at a predetermined frequency f0 when the ultrasonic vibration is transmitted, and a second vibrating section 32 which is configured to perform a second vibration at the same predetermined frequency f0 as in the first vibration when the ultrasonic vibration is transmitted. In the present embodiment, the first vibration transmitting member 21 becomes the first vibrating section 31 and the second vibration transmitting member 22 becomes the second vibrating section 32. Therefore, the ultrasonic vibrator 12, which is the ultrasonic generating portion, is attached to the first vibrating section 31.

In a state that the ultrasonic probe 12 is attached to the ultrasonic transmitting unit 3, the ultrasonic vibration generated in the ultrasonic vibrator 12 is transmitted to the first vibrating section 31. Then, in the first vibrating section 31, the ultrasonic vibration is transmitted from the distal direction toward the proximal direction. In consequence, the first vibrating section 31 performs the first vibration having first antinode positions A1, A2 and a first node position N1. The ultrasonic vibration is transmitted from the first vibrating section 31 to the second vibrating section 32. Then, in the second vibrating section 32, the ultrasonic vibration is transmitted from the proximal direction toward the distal direction. In consequence, the second vibrating section 32 performs the second vibration having second antinode positions A'1 to A'3 and second node positions N'1, N'2.

It is to be noted that the first vibration transmitting member 21 having a shape similar to that of the first vibrating section 31 vibrates at the predetermined frequency f0 even in a state that the second vibration transmitting member 22 is not attached, when the ultrasonic vibration is transmitted. Furthermore, the second vibration transmitting member 22 having a shape similar to that of the second vibrating section 32 vibrates at the predetermined frequency f0 even in the state that the second vibration transmitting member is not attached to the first vibration transmitting member 21, when the ultrasonic vibration is transmitted.

The first vibrating section 31 includes a first vibration main body portion 35. The first vibration main body portion 35 is continuous to a proximal direction side of the vibrator attaching portion 27. In the first vibration main body portion 35, a distal side relay portion 36 is provided. The distal side relay portion 36 is positioned at a proximal end of the first vibration main body portion 35 (a proximal end of the first vibrating section 31 in the present embodiment). Furthermore, inside the first vibrating section 31, a cavity portion 37 is formed along the longitudinal axis C. Therefore, the first vibrating section 31 is a tubular hollow section in which the cavity portion 37 is formed.

The second vibrating section 32 includes a second vibration main body portion 41. In the present embodiment, a proximal end of the second vibration main body portion 41 becomes a proximal end of the second vibrating section 32. In the second vibration main body portion 41, a proximal side relay portion 42 is disposed. The proximal side relay portion 42 is positioned at a distal end of the second vibration main body portion 41. In a state that the second vibration transmitting member 22 is attached to the first vibration transmitting member 21, the proximal side relay portion 42 abuts on the distal side relay portion 36 of the first vibrating section 31. That is, a position of the distal side relay portion 36 coincides with a position of the proximal side relay portion 42 in the directions parallel to the longitudinal axis C. When the proximal side relay portion 42 abuts on the distal side relay portion 36, the ultrasonic vibration can be transmitted from the first vibrating section 31 to the second vibrating section 32. It is to be noted that in the second vibrating section 32, an outer diameter of the second vibration main body portion 41 in a part located to the proximal direction side from the proximal side relay portion 42 is about the same as an outer diameter of the first vibration main body portion 35 of the first vibrating section 31.

Furthermore, the second vibrating section 32 includes a non-contact vibrating portion 43 extending from the proximal side relay portion 42 toward the distal direction side. A distal end of the non-contact vibrating portion 43 becomes a distal end of the second vibrating section 32. That is, the distal end of the second vibrating section 32 is positioned in the non-contact vibrating portion 43. The second vibration main body portion 41 is continuous with a proximal direction side of the non-contact vibrating portion 43.

In a state that the proximal side relay portion 42 abuts on the distal side relay portion 36, the non-contact vibrating portion 43 is inserted through the first vibrating section (the hollow section) 31. That is, the non-contact vibrating portion 43 is a columnar portion extending through the cavity portion 37 of the first vibrating section 31. The non-contact vibrating portion (the columnar portion) 43 extends from the distal side relay portion 36 positioned at the proximal end of the first vibrating section 31 toward the distal direction side. Furthermore, the non-contact vibrating portion extends up to a position located to the distal direction side from a distal end of the first vibrating section 31 through the cavity portion 37 of the first vibrating section 31. The non-contact vibrating portion 43 does not come in contact with the first vibrating section 31 when the non-contact vibrating portion is inserted through the first vibrating section (the hollow section) 31.

Figure 5:
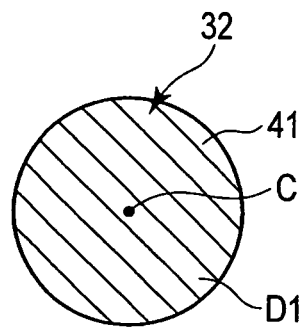
FIG. 5 is a sectional view along the line V-V of FIG. 3.
Figure 6:
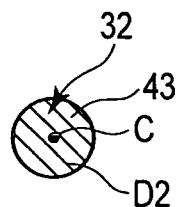
FIG. 6 is a sectional view along the line VI-VI of FIG. 3.

FIG. 5 is a sectional view along the line V-V of FIG. 3, and FIG. 6 is a sectional view along the line VI-VI of FIG. 3. As shown in FIG. 3 and FIG. 4, the second vibrating section 32 includes a sectional area changing portion 45. Due to the sectional area changing portion 45, at the proximal side relay portion 42, a sectional area perpendicular to the longitudinal axis C of the second vibrating section 32 changes. Therefore, a second sectional area D2 (see FIG. 6) perpendicular to the longitudinal axis C of the non-contact vibrating portion 43 (the second vibrating section 32) located to the distal direction side from the proximal side relay portion 42 is smaller than a first sectional area D1 (see FIG. 5) perpendicular to the longitudinal axis C of the second vibration main body portion 41 (the second vibrating section 32) located to the proximal direction side with respect to the proximal side relay portion 42.

Next, functions and effects of the ultrasonic transmitting unit 3 and the ultrasonic treatment device 1 will be described. When a treatment object such as a living tissue is treated by using the ultrasonic transmitting unit 3, a current of a predetermined value and a predetermined frequency is supplied from the current supply section 8 to the ultrasonic vibrator 12 via the electric wiring lines 13A, 13B by an operation in the input section 9. In consequence, the ultrasonic vibration is generated in the ultrasonic vibrator (the ultrasonic generating portion) 12, and the ultrasonic vibration is transmitted to the first vibrating section 31 of the ultrasonic transmitting unit 3. Furthermore, when the ultrasonic vibration is transmitted from the distal direction toward the proximal direction in the first vibrating section 31, the first vibrating section 31 performs the first vibration at the predetermined frequency f0.

The ultrasonic vibration transmitted to the first vibrating section 31 is transmitted to the second vibrating section 32. Furthermore, when the ultrasonic vibration is transmitted from the proximal direction toward the distal direction in the second vibrating section 32, the second vibrating section 32 performs the second vibration at the same predetermined frequency f0 as in the first vibration. A distal portion of the ultrasonic transmitting unit 3 (the second vibrating section 32) performs the treatment of the treatment target in a state that the ultrasonic transmitting unit 3 is vibrated. In this case, an amplitude of the ultrasonic vibration at the distal end of the ultrasonic transmitting unit 3 (the second vibrating section 32) becomes larger, so that the treatment of the treatment object is efficiently performed by using the ultrasonic vibration.

Here, the first vibration transmitting member 21 having the shape similar to that of the first vibrating section 31 vibrates at the predetermined frequency f0 even in the state that the second vibration transmitting member 22 is not attached, when the ultrasonic vibration is transmitted. That is, the first vibrating section 31 (the first vibration transmitting member 21) performs the first vibration at the predetermined frequency f0 even alone.

Figure 7:
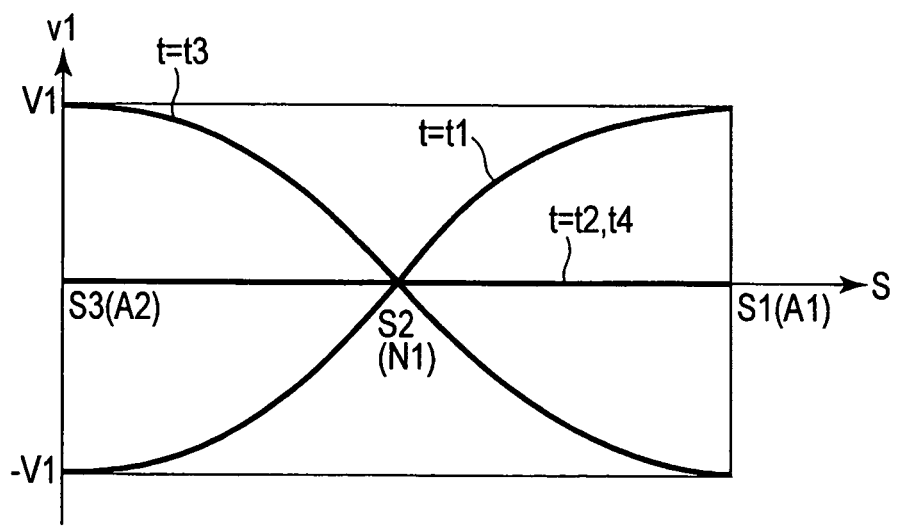
FIG. 7 is a schematic view showing a change of a first vibration with respect to a change of a position along a longitudinal axis in a first vibrating section, when the first vibrating section according to the first embodiment vibrates alone.

FIG. 7 is a view showing a change of a first vibration (v1) in accordance with a change of a position S along the longitudinal axis C in the first vibrating section 31 when the first vibrating section 31 alone vibrates. It is to be noted that FIG. 7 shows the first vibration (v1) at time t=t1, t2, t3, and t4. As shown in FIG. 3, FIG. 4 and FIG. 7, in the first vibration of the predetermined frequency f0, a position S1 which is the proximal end of the first vibration main body portion 35 (the proximal end of the first vibrating section 31) becomes the first antinode position A1. Furthermore, in the first vibration, a position S3 which is a distal end of the vibrator attaching portion 27 (the distal end of the first vibrating section 31) becomes the first antinode position A2. In the first vibrating section 31, the proximal end becomes the first antinode position A1 and the distal end becomes the first antinode position A2, so that the first vibrating section can vibrate at the predetermined frequency f0. Furthermore, a position S2 positioned at an intermediate position between the position S1 and the position S3 becomes the first node position N1 of the first vibration.

Here, the amplitude of the first vibration at each position (S) in the first vibrating section 31 along the longitudinal axis C is a first amplitude. In the first vibration of the first vibrating section 31 alone, the first amplitude at the first antinode positions A1, A2 has a magnitude V1. Furthermore, in the first vibrating section 31, the distal side relay portion 36 is positioned at the first antinode position A1. Here, the first antinode position A1 is one of the first antinode positions A1, A2, and becomes a relay antinode position where the distal side relay portion 36 is positioned.

Furthermore, the second vibration transmitting member 22 having a shape similar to that of the second vibrating section 32 vibrates at the predetermined frequency f0 even in a state that the second vibration transmitting member is not attached to the first vibration transmitting member 21, when the ultrasonic vibration is transmitted. That is, the second vibrating section 32 (the second vibration transmitting member 22) performs a second vibration at the predetermined frequency f0 even alone.

Figure 8:
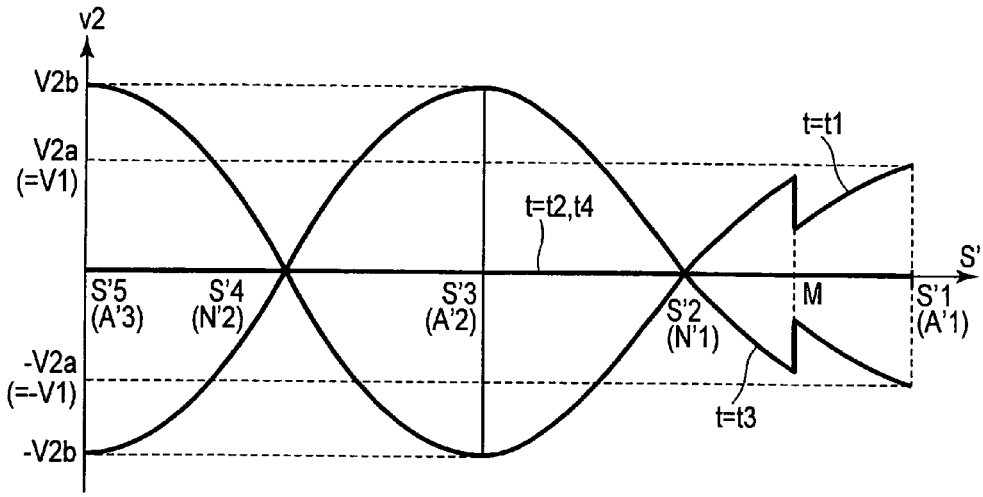
FIG. 8 is a schematic view showing a change of a second vibration in accordance with a change of a position along a longitudinal axis in a second vibrating section, when the second vibrating section according to the first embodiment vibrates alone.

FIG. 8 is a view showing a change of the second vibration (v2) with respect to a change of a position S' along the longitudinal axis C in the second vibrating section 32 when the second vibrating section 32 vibrates alone. It is to be noted that FIG. 8 shows the second vibration (v2) at time t=t1, t2, t3, and t4. As shown in FIG. 3, FIG. 4 and FIG. 8, in the second vibration at the predetermined frequency f0, a position S'1 which is the proximal end of the second vibration main body portion 41 (the proximal end of the second vibrating section 32) becomes the second antinode position A'1. Furthermore, in the second vibration, a position S'5 which is the distal end of the second vibrating section 32 (the distal end of the non-contact vibrating portion 43) becomes the second antinode position A'3. In the second vibrating section 32, the distal end becomes the second antinode position A'3 and the proximal end becomes the second antinode position A'1, so that the second vibrating section can vibrate at the predetermined frequency f0.

Furthermore, in the second vibrating section 32, positions S'2 to S'4 are positioned between the position S'1 and the position S'5 in the directions parallel to the longitudinal axis C. In the second vibration, the position S'3 becomes the second antinode position A'2. Furthermore, in the second vibration, the position S'2 becomes the second node position N'1 and the position S'4 becomes the second node position N'2. Here, the second antinode position A'3 positioned most distally among the second antinode positions A'1 to A'3 becomes a most distal antinode position.

Furthermore, the proximal side relay portion 42 is positioned at a middle position M different from the second antinode positions A'1 to A'3 and the second node positions N'1, N'2 of the second vibration. In the present embodiment, the middle position M is positioned between the second node position N'1 and the second antinode position A'1.

Here, an amplitude of the second vibration at each position (S') of the second vibrating section 32 along the longitudinal axis C is a second amplitude. In the second vibration of the second vibrating section 32 alone, the second amplitude at the second antinode position A'1 has a magnitude V2a. Furthermore, the second amplitude at the second antinode positions A'2, A'3 has a magnitude V2b. The magnitude V2a of the second amplitude at the second antinode position A'1 when the second vibrating section 32 alone vibrates is the same as the magnitude V1 of the first amplitude at the first antinode positions A1, A2 when the first vibrating section 31 alone vibrates.

Furthermore, in the proximal side relay portion 42 of the second vibrating section 32, a sectional area of the second vibrating section 32 perpendicular to the longitudinal axis C changes due to the sectional area changing portion 45. That is, the second sectional area D2 perpendicular to the longitudinal axis C of the non-contact vibrating portion 43 (the second vibrating section 32) positioned to the distal direction side with respect to the proximal side relay portion 42 is smaller than the first sectional area D1 perpendicular to the longitudinal axis C of the second vibration main body portion 41 (the second vibrating section 32) positioned to the proximal direction side from the proximal side relay portion 42. In the second vibrating section 32, the ultrasonic vibration is transmitted from the proximal direction toward the distal direction. Therefore, in the sectional area changing portion 45 (the proximal side relay portion 42), the amplitude of the ultrasonic vibration is enlarged. Therefore, the magnitude V2b of the second amplitude at the second antinode positions A'2, A'3 located to the distal direction side from the sectional area changing portion 45 is larger than the magnitude V2a of the second amplitude at the second antinode position A'1 located to the proximal direction side from the sectional area changing portion 45.

Furthermore, the ultrasonic transmitting unit 3 in which the second vibration transmitting member 22 is attached to the first vibration transmitting member 21 also vibrates at the predetermined frequency f0, when the ultrasonic vibration is transmitted. In this case, the first vibrating section 31 performs the first vibration at the predetermined frequency f0 and the second vibrating section 32 performs the second vibration at the predetermined frequency f0.

Figure 9:
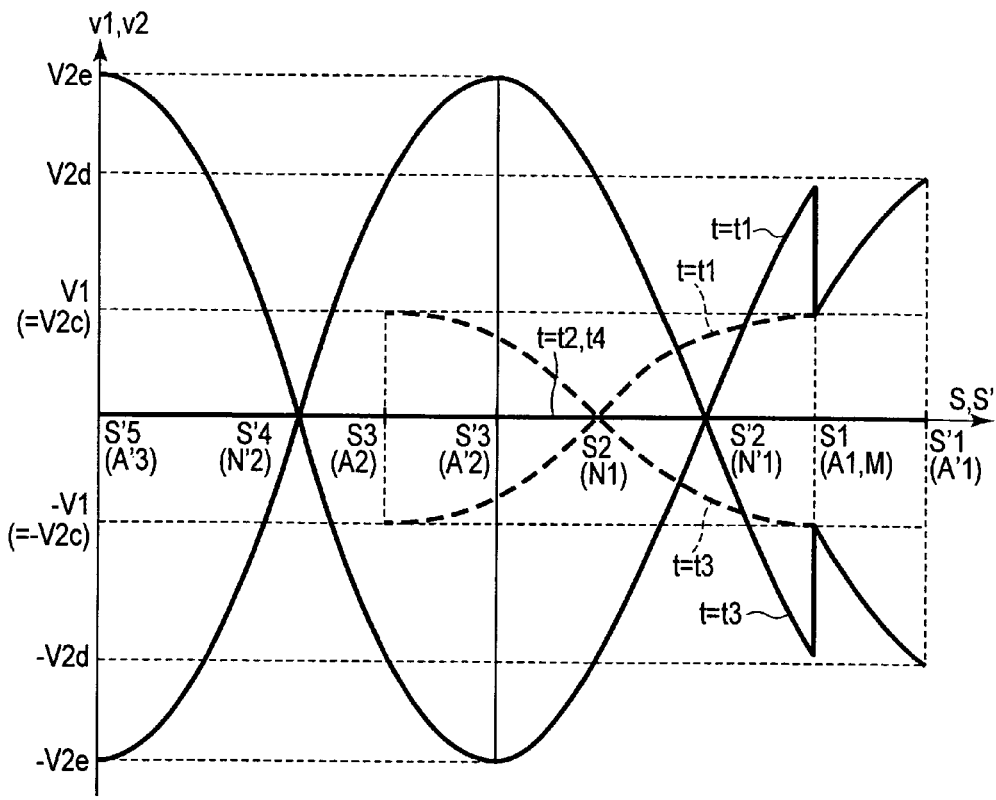
FIG. 9 is a schematic view showing the change of the first vibration and the change of the second vibration with respect to a change of a position along the longitudinal axis in the ultrasonic transmitting unit, when the ultrasonic transmitting unit according to the first embodiment vibrates.

FIG. 9 is a view showing the change of the first vibration (v1) and the change of the second vibration (v2) with respect to a change of the position (S, S') along the longitudinal axis C in the ultrasonic transmitting unit 3 when the ultrasonic transmitting unit 3, in which the second vibration transmitting member 22 is attached to the first vibration transmitting member 21, vibrates. It is to be noted that FIG. 9 shows the first vibration (v1) and the second vibration (v2) at time t=t1, t2, t3, and t4. Furthermore, FIG. 9 shows the first vibration of the first vibrating section 31 by a dotted line, and shows the second vibration of the second vibrating section 32 by a solid line.

As shown in FIG. 3, FIG. 4 and FIG. 9, also in a case where the ultrasonic transmitting unit 3 vibrates, the first vibrating section 31 performs the first vibration at the predetermined frequency f0 in the same manner as in a case where the first vibrating section 31 performs the first vibration alone. Therefore, the first antinode positions A1, A2 and the first node position N1 in the directions parallel to the longitudinal axis C are the same positions as the first antinode positions A1, A2 and the first node position N1 when the first vibrating section 31 alone performs the first vibration. Furthermore, also in a case where the ultrasonic transmitting unit 3 vibrates at the predetermined frequency f0, the first amplitude at the first antinode positions A1, A2 has the amplitude V1 in the same manner as in the case where the first vibrating section 31 vibrates alone.

Furthermore, in the case where the ultrasonic transmitting unit 3 vibrates, the second vibrating section 32 performs the second vibration at the predetermined frequency f0 in the same manner as in a case where the second vibrating section 32 alone performs the second vibration. Therefore, the second antinode positions A'1 to A'3 and the second node positions N'1, N'2 in the directions parallel to the longitudinal axis C are the same positions as the second antinode positions A'1 to A'3 and the second node positions N'1, N'2 in the case where the second vibrating section 32 performs the second vibration alone.

Here, in the ultrasonic transmitting unit 3, the ultrasonic vibration is transmitted from the first vibrating section 31 to the second vibrating section 32 via the distal side relay portion 36 and the proximal side relay portion 42. The distal side relay portion 36 is positioned at the first antinode position A1 of the first vibration and the proximal side relay portion 42 is positioned at the middle position M of the second vibration. In the ultrasonic transmitting unit 3, the proximal side relay portion 42 abuts on the distal side relay portion 36 and the first antinode position A1 coincides with the middle position M in the directions parallel to the longitudinal axis C.

FIG. 10 is a view showing a change of the first vibration with time at the relay antinode position (A1), when the ultrasonic transmitting unit 3 vibrates at the predetermined frequency f0. Furthermore, FIG. 11 is a view showing a change of the second vibration with time at the middle position M when the ultrasonic transmitting unit 3 vibrates at the predetermined frequency f0. As shown in FIG. 9 to FIG. 11, when the ultrasonic transmitting unit 3 vibrates, the first amplitude of the first vibration at the relay antinode position (A1) has the magnitude V1. Furthermore, the second amplitude of the second vibration at the middle position M has a magnitude V2c.

Here, the proximal side relay portion 42 abuts on the distal side relay portion 36, and the first antinode position A1 matches the middle position M in the directions parallel to the longitudinal axis C. Therefore, the magnitude V2c of the second amplitude at the middle position M is the same as the magnitude V1 of the first amplitude at the first antinode position A1 (, A2). Furthermore, the first vibration at the relay antinode position (the first antinode position) A1 and the second vibration at the middle position M have the same phase with respect to each other.

When the ultrasonic transmitting unit 3 vibrates, the magnitude V2c of the second amplitude at the middle position M different from the second antinode positions A'1 to A'3 becomes the same as the magnitude V1 of the first amplitude at the first antinode positions A1, A2. When the ultrasonic transmitting unit 3 vibrates, the second amplitude at the second antinode position A'1 has a magnitude V2d and the second amplitude at the second antinode positions A'2, A'3 has a magnitude V2e. In the second vibration, the second amplitude at the second antinode positions A'1 to A'3 is larger than the second amplitude at the middle position M. Therefore, when the ultrasonic transmitting unit 3 vibrates at the predetermined frequency f0, the magnitudes V2d, V2e of the second amplitude at the second antinode positions A'1 to A'3 of the second vibration are larger than the magnitude V1 of the first amplitude at the first antinode positions A1, A2 of the first vibration.

As described above, it is possible to enlarge the second amplitude of the ultrasonic vibration at the distal end of the second vibrating section 32 (the distal end of the ultrasonic transmitting unit 3) by a configuration other than the configuration to change the sectional area perpendicular to the longitudinal axis C of the ultrasonic transmitting unit 3. Furthermore, the outer diameter of the second vibration main body portion 41 located to the proximal direction side from the proximal side relay portion 42 in the second vibrating section 32 is about the same as the outer diameter of the first vibration main body portion 35 of the first vibrating section 31. Therefore, the outer diameter of the second vibration main body portion 41 does not become larger. Therefore, the outer diameter of the ultrasonic transmitting unit 3 is not increased, but the amplitude of the ultrasonic vibration is effectively enlarged. In consequence, the treatment of the treatment object is efficiently performed by using the ultrasonic vibration at the distal end of the ultrasonic transmitting unit 3, without increasing the outer diameter of the ultrasonic transmitting unit 3.

Furthermore, the ultrasonic vibration is transmitted from the distal direction toward the proximal direction in the first vibrating section 31. Then, the ultrasonic vibration is transmitted to the second vibrating section 32 through the distal side relay portion 36 and the proximal side relay portion 42. Then, in the second vibrating section 32, the ultrasonic vibration is transmitted from the proximal direction toward the distal direction. As described above, the ultrasonic vibration is transmitted, and hence it is not necessary to increase a dimension of the ultrasonic transmitting unit 3 in the directions parallel to the longitudinal axis C. Therefore, the amplitude of the ultrasonic vibration is effectively enlarged without increasing the dimension of the ultrasonic transmitting unit 3 in the directions parallel to the longitudinal axis C. In consequence, the treatment of the treatment target is efficiently performed by using the ultrasonic vibration at the distal end of the ultrasonic transmitting unit 3, without increasing the dimension of the ultrasonic transmitting unit 3 in the directions parallel to the longitudinal axis C.

Furthermore, in the second vibrating section 32, there are disposed the proximal side relay portion 42 on which the distal side relay portion 36 of the first vibrating section 31 abuts, and the non-contact vibrating portion 43 inserted through the cavity portion 37 of the first vibrating section (the hollow section) 31. Therefore, in the proximal side relay portion 42 of the second vibrating section 32, the sectional area of the second vibrating section 32 perpendicular to the longitudinal axis C changes due to the sectional area changing portion 45. That is, the second sectional area D2 perpendicular to the longitudinal axis C of the non-contact vibrating portion 43 (the second vibrating section 32) located to the distal direction side with respect to the proximal side relay portion 42 is smaller than the first sectional area D1 perpendicular to the longitudinal axis C of the second vibration main body portion 41 (the second vibrating section 32) located to the proximal direction side from the proximal side relay portion 42.

In the second vibrating section 32, the ultrasonic vibration is transmitted from the proximal direction toward the distal direction. Therefore, in the sectional area changing portion 45 (the proximal side relay portion 42), the amplitude of the ultrasonic vibration is further enlarged. That is, the magnitude V2e of the second amplitude at the second antinode positions A'2, A'3 located to the distal direction side from the sectional area changing portion 45 is larger than the magnitude V2d of the second amplitude at the second antinode position A'1 located to the proximal direction side from the sectional area changing portion 45. Therefore, the amplitude of the ultrasonic vibration is further effectively enlarged. It is to be noted that as described above, the outer diameter of the second vibration main body portion 41 located to the proximal direction side from the sectional area changing portion 45 is about the same as the outer diameter of the first vibration main body portion 35 of the first vibrating section 31. Therefore, the outer diameter of the ultrasonic transmitting unit 3 does not become larger due to the sectional area changing portion 45.

FIG. 12 shows an enlargement ratio E of the magnitude V2e of the second amplitude at the most distal antinode position A'3 of the second vibration with respect to the magnitude V1 of the first amplitude at the first antinode positions A1, A2 of the first vibration, when a position of the middle position M is changed along the longitudinal axis C in the second vibrating section 32. That is, the drawing shows the enlargement ratio E of the magnitude V2e of the second amplitude at the most distal antinode position (A'3) with respect to the magnitude V1 of the first amplitude at the first antinode positions A1, A2, when the position of the middle position M is changed between the second node position N'1 and the second antinode position A'1. Here, the second node position N'1 becomes a nearby node position positioned closest to the middle position M among the second node positions (N'1, N'2). Furthermore, the second antinode position A'1 is a nearby antinode position positioned closest to the middle position M among the second antinode positions (A'1 to A'3).

As described above, the magnitude V2c of the second amplitude at the middle position M is the same as the magnitude V1 of the first amplitude at the first antinode position A1 which is the relay antinode position. Therefore, regardless of the positional change of the middle position M along the longitudinal axis C, the magnitude V2c of the second amplitude at the middle position M is the same as the magnitude V1 of the first amplitude at the first antinode positions A1, A2. That is, the magnitude V2c of the second amplitude at the middle position M does not change in accordance with the positional change of the middle position M along the longitudinal axis C.

On the other hand, as the position of the middle position M comes closer to the nearby node position (N'1), a ratio E' of the magnitude V2e of the second amplitude at the most distal antinode position (the second antinode position) A'3 with respect to the magnitude V2c of the second amplitude at the middle position M becomes larger. The magnitude V1 of the first amplitude at the first antinode positions A1, A2 is the same as the magnitude V2c of the second amplitude at the middle position M. Therefore, as shown in FIG. 12, as the position of the middle position M comes closer to the nearby node position (N'1), the enlargement ratio E of the second amplitude at the most distal antinode position A'3 with respect to the first amplitude at the first antinode positions A1, A2 becomes larger. Here, a dimension along the longitudinal axis C between the nearby node position (N'1) and the middle position M is a first axis parallel dimension L1, and a dimension along the longitudinal axis C between the nearby antinode position (A'1) and the middle position M is a second axis parallel dimension L2. When the first axis parallel dimension L1 is smaller than the second axis parallel dimension L2, the enlargement ratio E of the second amplitude at the most distal antinode position A'3 to the first amplitude at the first antinode positions A1, A2 becomes larger. In the present embodiment, the first axis parallel dimension L1 and the second axis parallel dimension L2 are preferably set so that the enlargement ratio E is 3 or more. Therefore, the treatment of the treatment object is further efficiently performed by using the ultrasonic vibration.

It is to be noted that when the middle position M coincides with the second node position N'1 which is the nearby node position, the enlargement ratio E of the second amplitude at the most distal antinode position A'3 with respect to the first amplitude at the first antinode positions A1, A2 infinitely becomes larger, and the second amplitude of the ultrasonic vibration at the second antinode positions A'1 to A'3 infinitely becomes larger. When a position where the second amplitude infinitely becomes larger is generated in the ultrasonic transmitting unit 3, transmission properties of the ultrasonic vibration in the ultrasonic transmitting unit 3 disadvantageously deteriorate. On the other hand, when the middle position M matches the second antinode position A'1, the amplitude of the ultrasonic vibration is enlarged only by the sectional area changing portion 45. Therefore, the magnitude V2d of the second amplitude at the second antinode position A'1 is the same as the magnitude V1 of the first amplitude at the first antinode positions A1, A2. That is, the enlargement ratio E of the second amplitude at the most distal antinode position A'3 with respect to the first amplitude at the first antinode positions A1, A2 is the same as a ratio D1/D2 of the first sectional area D1 with respect to the second sectional area D2. As described above, the middle position M of the second vibration is different from the second antinode positions A'1 to A'3 and the second node positions N'1, N'2, and hence the second amplitude of the ultrasonic vibration at the distal end of the second vibrating section 32 (the distal end of the ultrasonic transmitting unit 3) is effectively enlarged.

As described above, in the ultrasonic transmitting unit 3, the second amplitude of the ultrasonic vibration at the distal end of the second vibrating section 32 (the distal end of the ultrasonic transmitting unit 3) can be increased without increasing the outer diameter and without increasing the dimension in the directions parallel to the longitudinal axis C. In consequence, the treatment of the treatment object can efficiently be performed by using the ultrasonic vibration without increasing the outer diameter of the ultrasonic transmitting unit 3 and without increasing the dimension in the directions parallel to the longitudinal axis C of the ultrasonic transmitting unit 3.

Modifications of First Embodiment

Furthermore, in the first embodiment, the first vibrating section 31 and the second vibrating section 32 are formed of the first vibration transmitting member 21 of the shape similar to that of the first vibrating section 31 and the second vibration transmitting member 22 of the shape similar to that of the second vibrating section 32, but it is not limited to this example. For example, as a first modification shown in FIG. 13, a first vibrating section 31 and a second vibrating section 32 may be formed of a third vibration transmitting member 51 and a fourth vibration transmitting member 52. In the present modification, an engagement groove 53 is provided in the third vibration transmitting member 51, and an engaging projection 55 is provided in the fourth vibration transmitting member 52. Furthermore, when the engaging projection 55 engages with the engagement groove 53, the fourth vibration transmitting member 52 is attached to the third vibration transmitting member 51 to form the ultrasonic transmitting unit 3.

In the present modification, the engaging projection 55 is positioned to a distal direction side with respect to a distal side relay portion 36 and a proximal side relay portion 42. Therefore, at a position located to the distal direction side from the distal side relay portion 36 and the proximal side relay portion 42, the fourth vibration transmitting member 52 is attached to the third vibration transmitting member 51. Therefore, in the present modification, the third vibration transmitting member 51 becomes a part of the first vibrating section 31. Furthermore, the fourth vibration transmitting member 52 forms a part of the first vibrating section 31 except the third vibration transmitting member 51 and forms the second vibrating section 32. Furthermore, in the present modification, at the position located to the distal direction side from the distal side relay portion 36 and the proximal side relay portion 42, the fourth vibration transmitting member 52 is attached to the third vibration transmitting member 51, and hence the proximal side relay portion 42 is continuous with the distal side relay portion 36.

Furthermore, in the present modification, a proximal end of the third vibration transmitting member 51 is positioned to the distal direction side from the distal side relay portion 36, and hence the proximal end of the third vibration transmitting member 51 is a position different from a first antinode position (a relay antinode position) A1 of a first vibration. Therefore, in a state that the fourth vibration transmitting member 52 is not attached, the third vibration transmitting member 51 does not vibrate at a predetermined frequency f0 even when ultrasonic vibration is transmitted. In the state that the fourth vibration transmitting member 52 is not attached, the third vibration transmitting member 51 does not vibrate, and hence an erroneous actuation is effectively prevented in a treatment in which the ultrasonic vibration is used.

It is to be noted that a distal end of the fourth vibration transmitting member 52 is positioned at a second antinode position A'3 of a second vibration, and a proximal end thereof is positioned at a second antinode position A'1 of the second vibration. Therefore, the fourth vibration transmitting member 52, to which the ultrasonic vibration is transmitted, vibrates at the predetermined frequency f0 even in a state that the fourth vibration transmitting member is not attached to the third vibration transmitting member 51.

Also in the present modification, the fourth vibration transmitting member 52 is attached to the third vibration transmitting member 51, so that the first vibrating section 31 and the second vibrating section 32 similar to those of the first embodiment are formed. Therefore, a second amplitude at the second antinode positions A'1 to A'3 of a second vibration is larger than a first amplitude at the first antinode positions A1, A2 of the first vibration.

Figure 14:
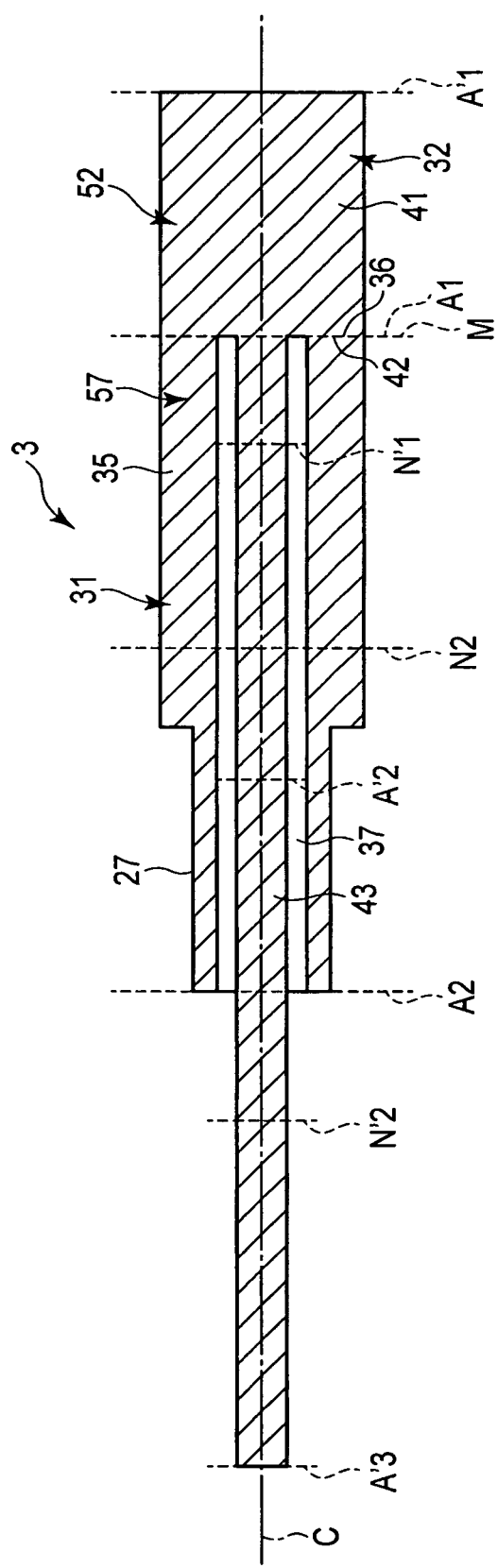
FIG. 14 is a sectional view schematically showing a configuration of an ultrasonic transmitting unit according to a second modification.

Furthermore, as a second modification shown in FIG. 14, a first vibrating section 31 and a second vibrating section 32 may integrally be formed of a fifth vibration transmitting member 57. In the present modification, the first vibrating section 31 and the second vibrating section 32 are integrally formed of the fifth vibration transmitting member 57, and hence a proximal side relay portion 42 is continuous with a distal side relay portion 36. Also in the present modification, the first vibrating section 31 and the second vibrating section 32 similar to those of the first embodiment are formed, and hence a second amplitude at second antinode positions A'1 to A'3 of a second vibration is larger than a first amplitude at first antinode positions A1, A2 of a first vibration.

Figure 15:
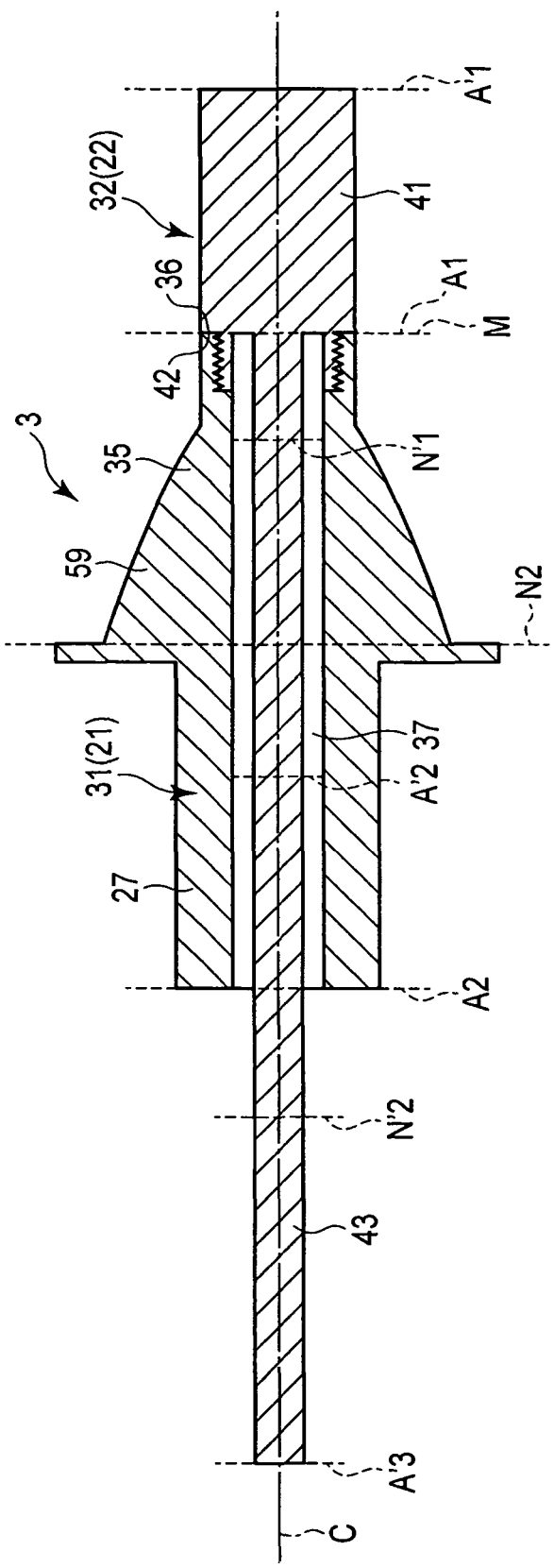
FIG. 15 is a sectional view schematically showing a configuration of an ultrasonic transmitting unit according to a third modification.

Furthermore, as a third modification shown in FIG. 15, a horn portion 59 in which a sectional area perpendicular to a longitudinal axis C changes may be provided in a first vibration main body portion 35. In the horn portion 59, the sectional area of a first vibrating section 31 which is perpendicular to the longitudinal axis C decreases from a distal direction toward a proximal direction.

FIG. 16 is a view showing a change of a first vibration (v1) with respect to a change of a position S along the longitudinal axis C in the first vibrating section 31, when an ultrasonic transmitting unit 3 of the present modification vibrates at a predetermined frequency f0. As shown in FIG. 16, the horn portion 59 is provided, and a first amplitude V1$b$ at a first antinode position (a relay antinode position) A1 located to a proximal direction side from the horn portion 59 is therefore larger than a first amplitude V1$a$ at a first antinode position A2 located to a distal direction side from the horn portion 59. Therefore, in the present modification, the amplitude of ultrasonic vibration at a distal end of the ultrasonic transmitting unit 3 (a distal end of a second vibrating section 32) is further effectively enlarged.

Second Embodiment

Next, a second embodiment of the present invention will be described with reference to FIG. 17 to FIG. 21. In the second embodiment, the configuration of the first embodiment is modified as follows. It is to be noted that the same part as in the first embodiment is denoted with the same reference numerals, and description thereof is omitted.

Figure 17:
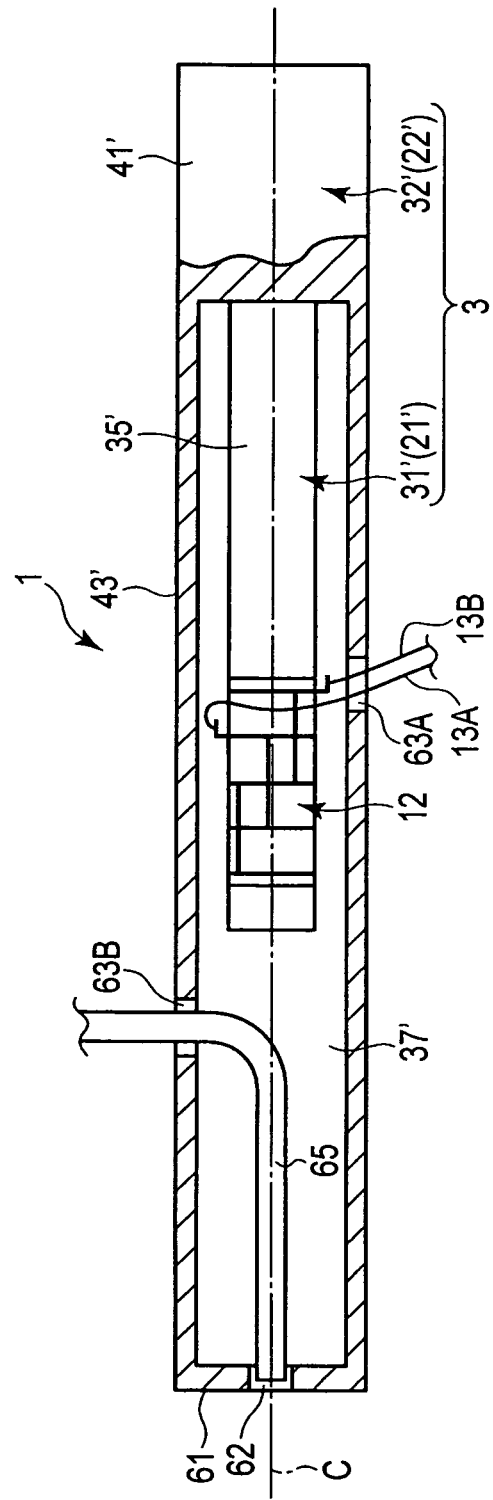
FIG. 17 is a sectional view schematically showing an ultrasonic treatment device according to a second embodiment.
Figure 18:
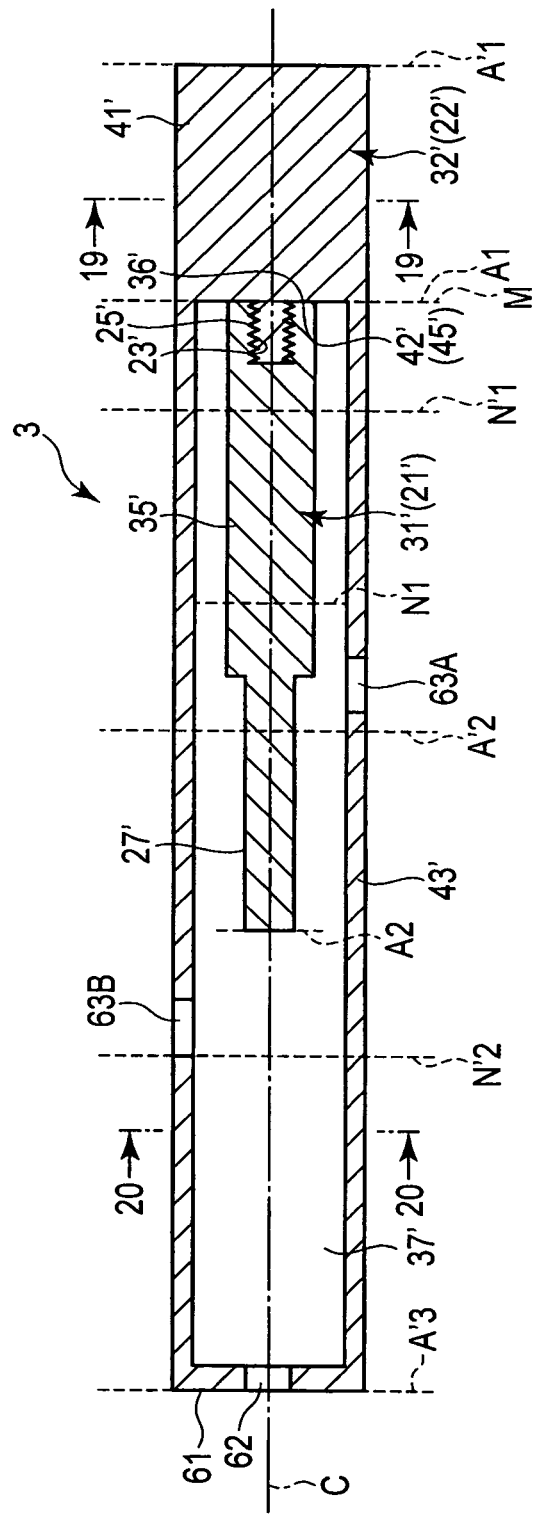
FIG. 18 is a sectional view schematically showing an ultrasonic transmitting unit according to the second embodiment.

FIG. 17 is a view showing an ultrasonic treatment device 1 of the present embodiment, and FIG. 18 is a view showing an ultrasonic transmitting unit 3. As shown in FIG. 17 and FIG. 18, the ultrasonic transmitting unit 3 includes a first vibration transmitting member 21' and a second vibration transmitting member 22'. A proximal end of the second vibration transmitting member 22' becomes a proximal end of the ultrasonic transmitting unit 3. Furthermore, a distal end of the second vibration transmitting member 22' becomes a distal end of the ultrasonic transmitting unit 3. An internal thread portion 23' is formed in a proximal portion of the first vibration transmitting member 21'. Furthermore, an external thread portion 25' is formed in the second vibration transmitting member 22'. The internal thread portion 23' is screwed to the external thread portion 25', and the first vibration transmitting member 21' is thereby attached to the second vibration transmitting member 22'. Furthermore, the second vibration transmitting member 22' is attached to a vibrator case 2.

The ultrasonic transmitting unit 3 includes a first vibrating section 31' which is configured to perform a first vibration at a predetermined frequency f0 when ultrasonic vibration is transmitted, and a second vibrating section 32' which is configured to perform a second vibration at the same predetermined frequency f0 as in the first vibration when the ultrasonic vibration is transmitted. In the present embodiment, the first vibration transmitting member 21' becomes the first vibrating section 31' and the second vibration transmitting member 22' becomes the second vibrating section 32'. An ultrasonic vibrator 12 which is an ultrasonic generating portion is attached to the first vibrating section 31'.

Similarly to the first vibrating section 31 of the first embodiment, in the first vibrating section 31', the ultrasonic vibration is transmitted from a distal direction toward a proximal direction. In consequence, the first vibrating section 31' performs the first vibration having first antinode positions A1, A2 and a first node position N1. Furthermore, similarly to the second vibrating section 32 of the first embodiment, in the second vibrating section 32', the ultrasonic vibration is transmitted from the proximal direction toward the distal direction. In consequence, the second vibrating section 32' performs the second vibration having second antinode positions A'1 to A'3 and second node positions N'1, N'2.

Similarly to the first vibrating section 31 of the first embodiment, the first vibrating section 31' includes a first vibration main body portion 35' and a vibrator attaching portion 27'. Furthermore, a distal side relay portion 36' is positioned at a proximal end of the first vibration main body portion 35' (a proximal end of the first vibrating section 31' in the present embodiment). However, in the present embodiment, differing from the first vibrating section 31 of the first embodiment, a cavity portion 37 is not formed inside the first vibrating section 31'. Therefore, the first vibrating section 31' is a columnar section.

Furthermore, similarly to the second vibrating section 32 of the first embodiment, the second vibrating section 32' includes a second vibration main body portion 41' and a non-contact vibrating portion 43'. In the present embodiment, a proximal end of the second vibration main body portion 41' becomes a proximal end of the second vibrating section 32'. Furthermore, a proximal side relay portion 42' is positioned at a distal end of the second vibration main body portion 41'. In a state that the second vibration transmitting member 22' is attached to the first vibration transmitting member 21', the proximal side relay portion 42' abuts on the distal side relay portion 36' of the first vibrating section 31'. The proximal side relay portion 42' abuts on the distal side relay portion 36', so that the ultrasonic vibration can be transmitted from the first vibrating section 31' to the second vibrating section 32'.

Furthermore, also in the second vibrating section 32', a distal end of the non-contact vibrating portion 43' becomes a distal end of the second vibrating section 32' in the same manner as in the second vibrating section 32 of the first embodiment. A cavity portion 37' is formed inside the non-contact vibrating portion 43', differing from the non-contact vibrating portion 43 of the first embodiment. That is, the non-contact vibrating portion 43' is a hollow portion inside which the cavity portion 37' is formed. Furthermore, the first vibrating section 31' which is the columnar section is disposed in the cavity portion 37'. Also in the present embodiment, similarly to the non-contact vibrating portion 43 of the first embodiment, the non-contact vibrating portion (the hollow portion) 43' extends up to a part located to a distal direction side from the distal end of the first vibrating section 31'.

Furthermore, the non-contact vibrating portion 43' does not come in contact with the first vibrating section 31'. It is to be noted that an outer diameter of the second vibration main body portion 41' located to the proximal direction side from the proximal side relay portion 42' in the second vibrating section 32' is about the same as an outer diameter of the non-contact vibrating portion 43' of the second vibrating section 32'.

FIG. 19 is a sectional view along the line 19-19 of FIG. 18, and FIG. 20 is a sectional view along the line 20-20 of FIG. 18. As shown in FIG. 16 and FIG. 17, the second vibrating section 32' includes a sectional area changing portion 45'. Due to the sectional area changing portion 45', in the proximal side relay portion 42', a sectional area perpendicular to a longitudinal axis C of the second vibrating section 32' changes. Therefore, a second sectional area D'2 (see FIG. 20) perpendicular to the longitudinal axis C of the non-contact vibrating portion 43' (the second vibrating section 32') located to the distal direction side from the proximal side relay portion 42' is smaller than a first sectional area D'1 (see FIG. 19) perpendicular to the longitudinal axis C of the second vibration main body portion 41' (the second vibrating section 32') located to the proximal direction side with respect to the proximal side relay portion 42'.

FIG. 21 is a view of FIG. 17 seen from the distal direction. As shown in FIG. 17, FIG. 18 and FIG. 21, the second vibrating section 32' includes a distal surface 61 which forms the distal end of the ultrasonic transmitting unit 3 (the second vibrating section 32'). On the distal surface 61, there is formed an open portion 62 which allows the outside of the second vibrating section 32' to communicate with the cavity portion 37'. An area of the open portion 62 is smaller than a sectional area perpendicular to the longitudinal axis C of the cavity portion 37'. Therefore, a surface area P of the distal surface 61 is larger than the second sectional area D'2 perpendicular to the longitudinal axis C of the non-contact vibrating portion 43' (the second vibrating section 32') located to the distal direction side from the proximal side relay portion 42'.

Furthermore, on an outer peripheral portion of the non-contact vibrating portion 43', there are formed opening holes 63A, 63B which allow the outside of the second vibrating section 32' to communicate with the cavity portion 37'. Electric wiring lines 13A, 13B each having one end connected to the ultrasonic vibrator 12 pass through the opening hole 63A from the cavity portion 37' to extend to the outside of the second vibrating section 32'. Furthermore, the other end of each of the electric wiring lines 13A, 13B is connected to a current supply section 8 of a power source unit 7 through an inside of the vibrator case 2 and an inside of a cable 6.

Furthermore, the open portion 62 of the distal surface 61 of the second vibrating section 32' is connected to one end of a suction tube 65. The suction tube 65 extends through the cavity portion 37' and passes through the opening hole 63B to extend to the outside of the second vibrating section 32'. Furthermore, the other end of the suction tube 65 is connected to a suction unit (not shown).

Next, functions and effects of the ultrasonic transmitting unit 3 and the ultrasonic treatment device 1 will be described. When a treatment object such as a living tissue is treated by using the ultrasonic transmitting unit 3, a current is supplied from the current supply section 8 to the ultrasonic vibrator 12 via the electric wiring lines 13A, 13B by an operation in an input section 9. In consequence, the ultrasonic vibration is generated in the ultrasonic vibrator (an ultrasonic generating portion) 12, and the ultrasonic vibration is transmitted to the first vibrating section 31' of the ultrasonic transmitting unit 3. Furthermore, similarly to the first embodiment, when the ultrasonic vibration is transmitted from the distal direction toward the proximal direction in the first vibrating section 31', the first vibrating section 31' performs the first vibration at the predetermined frequency f0.

The ultrasonic vibration transmitted to the first vibrating section 31' is transmitted to the second vibrating section 32'. Furthermore, similarly to the first embodiment, when the ultrasonic vibration is transmitted from the proximal direction toward the distal direction in the second vibrating section 32', the second vibrating section 32' performs the second vibration at the same predetermined frequency f0 as in the first vibration. A distal portion of the ultrasonic transmitting unit 3 (the second vibrating section 32') performs the treatment of the treatment target in a state that the ultrasonic transmitting unit 3 is vibrated. That is, in the distal surface 61 of the second vibrating section 32', the living tissue is shattered and emulsified by using a cavitation phenomenon. In this case, an amplitude of the ultrasonic vibration at the distal surface 61 of the ultrasonic transmitting unit 3 (the second vibrating section 32') becomes larger, so that the living tissue is efficiently shattered and emulsified, and the treatment of the treatment object is efficiently performed by using the ultrasonic vibration.

Then, the suction unit (not shown) is driven, and the shattered and emulsified living tissue is suctioned from the open portion 62 of the distal surface 61. The suctioned living tissue passes through the suction tube 65, and is suctioned and collected by the suction unit. As described above, an ultrasonic suction treatment is performed.

Similarly to the first embodiment, also in the present embodiment, in the first vibrating section 31', the distal side relay portion 36' is positioned at the relay antinode position A1 which is one of the first antinode positions A1, A2. Furthermore, a first amplitude at the first antinode positions A1, A2 in the first vibration has a magnitude V1. Furthermore, similarly to the first embodiment, in the second vibrating section 32', the proximal side relay portion 42' is positioned at a middle position M different from the second antinode positions A'1 to A'3 and the second node positions N'1, N'2 of the second vibration. Furthermore, in the second vibration, a second amplitude at the second antinode position A'1 has a magnitude V2$d$, and the second amplitude at the second antinode positions A'2, A'3 has a magnitude V2$e$.

Furthermore, similarly to the first embodiment, also in the present embodiment, at the middle position M (the first antinode position A1), the proximal side relay portion 42' abuts on the distal side relay portion 36' and the ultrasonic vibration is transmitted from the first vibrating section 31' to the second vibrating section 32'. Therefore, a magnitude V2$c$ of the second amplitude at the middle position M is the same as the magnitude V1 of the first amplitude at the first antinode position A1 (, A2). Furthermore, the first vibration at the relay antinode position (the first antinode position) A1 and the second vibration at the middle position M have the same phase with respect to each other. In consequence, in the second vibration, the magnitude V2$c$ of the second amplitude at the middle position M different from the second antinode positions A'1 to A'3 is the same as the magnitude V1 of the first amplitude at the first antinode positions A1, A2 of the first vibration. Therefore, the second amplitude at the second antinode positions A'1 to A'3 of the second vibration is larger than the first amplitude at the first antinode positions A1, A2 of the first vibration.

As described above, it is possible to enlarge the second amplitude of the ultrasonic vibration in the distal surface 61 of the second vibrating section 32' (the distal end of the ultrasonic transmitting unit 3) by a configuration other than the configuration to change the sectional area perpendicular to the longitudinal axis C. Furthermore, the outer diameter of the second vibration main body portion 41' located to the proximal direction side from the proximal side relay portion 42' in the second vibrating section 32' is about the same as the outer diameter of the non-contact vibrating portion 43' of the second vibrating section 32'. Therefore, the outer diameter of the second vibration main body portion 41' does not become larger. Therefore, the outer diameter of the ultrasonic transmitting unit 3 is not increased, but the amplitude of the ultrasonic vibration is effectively enlarged. In consequence, the treatment of the treatment object is efficiently performed by using the ultrasonic vibration at the distal end of the ultrasonic transmitting unit 3, without increasing the outer diameter of the ultrasonic transmitting unit 3.

Furthermore, similarly to the first embodiment, the ultrasonic vibration is transmitted from the distal direction toward the proximal direction in the first vibrating section 31'. Furthermore, the ultrasonic vibration is transmitted to the second vibrating section 32' through the distal side relay portion 36' and the proximal side relay portion 42'. Furthermore, in the second vibrating section 32', the ultrasonic vibration is transmitted from the proximal direction toward the distal direction. As described above, the ultrasonic vibration is transmitted, and hence it is not necessary to increase a dimension in directions parallel to the longitudinal axis C of the ultrasonic transmitting unit 3. Therefore, the amplitude of the ultrasonic vibration is effectively enlarged without increasing the dimension in the directions parallel to the longitudinal axis C of the ultrasonic transmitting unit 3. In consequence, the treatment of the treatment object is efficiently performed by using the ultrasonic vibration at the distal end of the ultrasonic transmitting unit 3, without increasing the dimension in the directions parallel to the longitudinal axis C of the ultrasonic transmitting unit 3.

Furthermore, in the proximal side relay portion 42' of the second vibrating section 32', the sectional area of the second vibrating section 32' which is perpendicular to the longitudinal axis C changes due to the sectional area changing portion 45'. That is, the second sectional area D'2 perpendicular to the longitudinal axis C of the non-contact vibrating portion 43' (the second vibrating section 32') located to the distal direction side from the proximal side relay portion 42' is smaller than the first sectional area D'1 perpendicular to the longitudinal axis C of the second vibration main body portion 41' (the second vibrating section 32') located to the proximal direction side from the proximal side relay portion 42'. In the second vibrating section 32', the ultrasonic vibration is transmitted from the proximal direction toward the distal direction. Therefore, in the sectional area changing portion 45' (the proximal side relay portion 42'), the amplitude of the ultrasonic vibration is further enlarged. That is, the magnitude V2$e$ of the second amplitude at the second antinode positions A'2, A'3 positioned to the distal direction side from the sectional area changing portion 45' is larger than the magnitude V2$d$ of the second amplitude at the second antinode position A'1 positioned to the proximal direction side from the sectional area changing portion 45'. Therefore, the amplitude of the ultrasonic vibration is further effectively enlarged.

Furthermore, the surface area P of the distal surface 61 of the ultrasonic transmitting unit 3 is larger than the second sectional area D'2 perpendicular to the longitudinal axis C of the non-contact vibrating portion 43' (the second vibrating section 32') located to the distal direction side from the proximal side relay portion 42'. The surface area P of the distal surface 61 becomes larger, so that the cavitation phenomenon due to the ultrasonic vibration is efficiently generated. In consequence, the living tissue is further efficiently shattered and emulsified, and the treatment of the treatment object is further efficiently performed by using the ultrasonic vibration.

As described above, in the ultrasonic transmitting unit 3, the magnitude V2*e* of the second amplitude of the ultrasonic vibration in the distal surface 61 of the second vibrating section 32' (the distal end of the ultrasonic transmitting unit 3) can be increased without increasing the outer diameter and without increasing the dimension in the directions parallel to the longitudinal axis C. In consequence, the treatment of the treatment object can efficiently be performed by using the ultrasonic vibration without increasing the outer diameter of the ultrasonic transmitting unit 3 and without increasing the dimension in the directions parallel to the longitudinal axis C of the ultrasonic transmitting unit 3.

(Other Modifications)

Furthermore, in the abovementioned embodiments, the first vibrating section (31; 31') has two first antinode positions A1, A2 and one first node position N1, and the second vibrating section (32; 32') has three second antinode positions A'1 to A'3 and two second node positions N'1, N'2, but the numbers of the first antinode positions A1, A2, the first node position N1, the second antinode positions A'1 to A'3 and the second node positions N'1, N'2 are not limited to this example. That is, in the first vibrating section (31; 31'), the distal end and the proximal end may become the first antinode positions (A1, A2) of the first vibration. Furthermore, in the second vibrating section (32; 32'), the distal end and the proximal end may become the second antinode positions (A'1 to A'3) of the second vibration. In consequence, the first vibrating section (31; 31') and the second vibrating section (32; 32'), to which the ultrasonic vibration is transmitted, vibrate at the predetermined frequency f0.

From the abovementioned embodiments and modifications, the distal side relay portion (36; 36') may be provided in the first vibration main body portion (35; 35') of the first vibrating section (31; 31'), and the distal side relay portion (36; 36') may be positioned at the relay antinode position A1, which is one of the first antinode positions (A1, A2) of the first vibration. Furthermore, the proximal side relay portion (42; 42') may be provided in the second vibration main body portion (41; 41') of the second vibrating section (32; 32') in a state that the proximal side relay portion is continuous with the distal side relay portion (36; 36') of the first vibrating section (31; 31') or abuts on the distal side relay portion (36; 36'), and the proximal side relay portion (42; 42') may be positioned at the middle position M different from the second antinode positions (A'1 to A'3) and the second node positions (N'1, N'2) of the second vibration. Furthermore, the non-contact vibrating portion (43; 43') in which the distal end of the second vibrating section (32; 32') is positioned may be provided in the second vibrating section (32; 32'), and the non-contact vibrating portion (43; 43') may extend from the proximal side relay portion (42; 42') toward the distal direction side in a state that the non-contact vibrating portion is not in contact with the first vibrating section (31; 31'). Furthermore, the non-contact vibrating portion (43; 43') may extend up to a part locate to the distal direction side from the distal end of the first vibrating section (31; 31').

According to the abovementioned configuration, the ultrasonic vibration is transmitted from the distal direction toward the proximal direction in the first vibrating section (31; 31'). Furthermore, the ultrasonic vibration is transmitted from the first vibrating section (31; 31') to the second vibrating section (32; 32') via the distal side relay portion (36; 36') and the proximal side relay portion (42; 42'). Furthermore, in the second vibrating section (32; 32'), the ultrasonic vibration is transmitted from the proximal direction toward the distal direction. In this case, the second amplitude of the second vibration at the second antinode positions (A'1 to A'3) of the second vibrating section (32; 32') is larger than the first amplitude of the first vibration at the first antinode positions (A1, A2) of the first vibrating section (31; 31').

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic transmitting unit comprising:
a first vibrating section which extends from its proximal end to its distal end along a longitudinal axis;
a second vibrating section which extends from its proximal end to its distal end along the longitudinal axis, the distal end of the second vibrating portion being exposed with respect to an outside, wherein a proximal side with respect to the distal end of the first vibrating section and a distal side with respect to the proximal end of the second vibrating section form a continuous relay portion;
a non-contact vibrating portion which is provided in the second vibrating portion, and which extends from the relay portion toward the distal side in a state that the non-contact vibrating portion is not in contact with the first vibrating section, the non-contact vibrating portion forming the distal end of the second vibrating portion, protruding toward the distal side with respect to the distal end of the first vibrating section, and providing a treatment portion for transmitting the vibration to a tissue; and
an ultrasonic vibrator which is attached to the first vibrating section, and which is located on the distal side with respect to the relay portion, the ultrasonic vibrator being configured to generate an ultrasonic vibration, wherein
the first vibrating section is configured to transmit the ultrasonic vibration from the ultrasonic vibrator to the relay portion toward the proximal side so that the first vibrating section vibrates at a predetermined frequency,
the first vibrating section has first antinodes and at least one first node and one of the first anti nodes being positioned at the relay portion when the first vibrating section vibrates at the predetermined frequency,
the ultrasonic vibration is transmitted from the first vibrating section to the second vibrating section through only the relay portion,
the second vibrating section is configured to transmit the ultrasonic vibration from the relay portion to the distal end of the second vibration section through non-contact vibrating portion toward the distal side so that the second vibrating section vibrates at the same predetermined frequency as the first vibrating section,
the second vibrating section has second antinodes and at least one second node and all of the second antinodes and the at least one second node being positioned away from the relay portion when the second vibrating section vibrates at the predetermined frequency, and
an amplitude at the relay portion in the first vibrating section is the same as an amplitude at the relay portion in the second vibrating section when the first vibrating section and the second vibrating section vibrate at the predetermined frequency.

2. The ultrasonic transmitting unit of claim 1, wherein an amplitude at each of the second antinodes in the second vibrating section is larger than an amplitude at each of the first antinodes in the first vibrating section when the first vibrating section and the second vibrating section vibrate at the predetermined frequency.

3. The ultrasonic transmitting unit of claim 1, wherein the second vibrating section includes a sectional area changing portion which changes a sectional area perpendicular to the longitudinal axis at the relay portion, and by which a sectional area perpendicular to the longitudinal axis of the second vibrating section in the non-contact vibrating portion located on the distal side from the relay portion is smaller than a sectional area perpendicular to the longitudinal axis in a part of the second vibrating section located on the proximal side from the relay portion.

4. The ultrasonic transmitting unit of claim 3, wherein the first vibrating section is a hollow section inside which a cavity portion is formed, and the non-contact vibrating portion of the second vibrating section is a columnar portion extending through the cavity portion.

5. The ultrasonic transmitting unit of claim 3, wherein the non-contact vibrating portion of the second vibrating section is a hollow portion inside which a cavity portion is formed, and the first vibrating section is a columnar section disposed in the cavity portion.

6. The ultrasonic transmitting unit of claim 1, wherein a first dimension in a direction along the longitudinal axis between the relay portion and a second node closest to the relay portion among the at least one second node is smaller than a second dimension in the direction along the longitudinal axis between the relay portion and a second antinode closest to the relay portion among the second antinodes when the first vibrating section and the second vibrating section vibrate at the predetermined frequency.

7. An ultrasonic transmitting unit comprising:
    a first vibrating section which extends from its proximal end to its distal end along a longitudinal axis;
    a second vibrating section which extends from its proximal end to its distal end along the longitudinal axis, the distal end of the second vibrating portion being exposed with respect to an outside;
    a relay portion at which the second vibrating section is continuous with the first vibrating section or abuts on the first vibrating section, and which is located on a proximal side with respect to the distal end of the first vibrating section and located on a distal side with respect to the proximal end of the second vibrating section;
    a non-contact vibrating portion which is provided in the second vibrating portion, and which extends from the relay portion toward the distal side in a state that the non-contact vibrating portion is not in contact with the first vibrating section, the non-contact vibrating portion forming the distal end of the second vibrating portion, protruding toward the distal side with respect to the distal end of the first vibrating section, and providing a treatment portion for transmitting the vibration to a tissue; and
    an ultrasonic vibrator which is attached to the first vibrating section, and which is located on the distal side with respect to the relay portion, the ultrasonic vibrator being configured to generate an ultrasonic vibration, wherein
    the first vibrating section is configured to transmit the ultrasonic vibration from the ultrasonic vibrator to the relay portion toward the proximal side so that the first vibrating section vibrates at a predetermined frequency,
    the first vibrating section has first antinodes and at least one first node and one of the first anti nodes being positioned at the relay portion when the first vibrating section vibrates at the predetermined frequency,
    the ultrasonic vibration is transmitted from the first vibrating section to the second vibrating section through only the relay portion,
    the second vibrating section is configured to transmit the ultrasonic vibration from the relay portion to the distal end of the second vibration section through non-contact vibrating portion toward the distal side so that the second vibrating section vibrates at the same predetermined frequency as the first vibrating section,
    the second vibrating section has second antinodes and at least one second node and all of the second antinodes and the at least one second node being positioned away from the relay portion when the second vibrating section vibrates at the predetermined frequency, and
    an amplitude at the relay portion in the first vibrating section is the same as an amplitude at the relay portion in the second vibrating section when the first vibrating section and the second vibrating section vibrate at the predetermined frequency so that the ultrasonic vibration transmitted from the first vibrating section toward the second vibrating section is amplified at the relay portion.

8. An ultrasonic transmitting unit comprising:
    a first vibrating section which extends from its proximal end to its distal end along a longitudinal axis;
    a second vibrating section which extends from its proximal end to its distal end along the longitudinal axis, the distal end of the second vibrating portion being exposed with respect to an outside;
    a relay portion at which the second vibrating section is continuous with the first vibrating section or abuts on the first vibrating section, and which is located on a proximal side with respect to the distal end of the first vibrating section and located on a distal side with respect to the proximal end of the second vibrating section;
    a non-contact vibrating portion which is provided in the second vibrating portion, and which extends from the relay portion toward the distal side in a state that the non-contact vibrating portion is not in contact with the first vibrating section, the non-contact vibrating portion forming the distal end of the second vibrating portion, protruding toward the distal side with respect to the distal end of the first vibrating section, and providing a treatment portion for transmitting the vibration to a tissue; and
    an ultrasonic vibrator which is attached to the first vibrating section, and which is located on the distal side with respect to the relay portion, the ultrasonic vibrator being configured to generate an ultrasonic vibration, wherein
    the first vibrating section is configured to transmit the ultrasonic vibration from the ultrasonic vibrator to the relay portion toward the proximal side so that the first vibrating section vibrates at a predetermined frequency,
    the first vibrating section has first antinodes and at least one first node and one of the first anti nodes being positioned at the relay portion when the first vibrating section vibrates at the predetermined frequency, the ultrasonic vibration is transmitted from the first vibrating section to the second vibrating section through only the relay portion, the second vibrating section is configured to transmit the ultrasonic vibration from the relay portion to the distal end of the second vibration section through non-contact vibrating portion toward the distal side so that the second vibrating section vibrates at the same predetermined frequency as the first vibrating section, the second vibrating section has second antinodes and at least one second node and all of the second antinodes and the at least one second node being positioned away from the relay portion when the second vibrating section vibrates at the predetermined frequency, an amplitude at the relay portion in the first vibrating section is the same as an amplitude at the relay portion in the second vibrating section when the first vibrating section and the second vibrating section vibrate at the predetermined frequency, a first dimension from the distal end to the proximal end in the first vibrating section in the direction along the longitudinal axis is the same as one of integral multiples of a half wavelength of the ultrasonic vibration at the predetermined frequency, a second dimension from the distal end to the proximal end in the second vibrating section in the direction along the longitudinal axis is the same as another one of the integral multiples of the half wavelength of the ultrasonic vibration at the predetermined frequency, and is larger than the first dimension, and a third dimension from the distal end of the second vibrating section to the relay portion in the direction along the longitudinal axis is different from integral multiples of a quarter wavelength of the ultrasonic vibration at the predetermined frequency.

* * * * *